United States Patent
Tsujii

(10) Patent No.: US 7,123,683 B2
(45) Date of Patent: Oct. 17, 2006

(54) RADIOGRAPHING APPARATUS AND METHOD

(75) Inventor: Osamu Tsujii, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/442,338

(22) Filed: May 20, 2003

(65) Prior Publication Data

US 2003/0219101 A1    Nov. 27, 2003

(30) Foreign Application Priority Data

May 22, 2002 (JP) .............................. 2002-148003
Apr. 30, 2003 (JP) .............................. 2003-125821

(51) Int. Cl.
*A61B 6/00* (2006.01)
(52) U.S. Cl. ............................ 378/26; 378/196; 378/21
(58) Field of Classification Search ............ 378/21–27, 378/196–197
See application file for complete search history.

(56) References Cited

U.S. PATENT DOCUMENTS

| | | | |
|---|---|---|---|
| 4,160,906 A * | 7/1979 | Daniels et al. ................. | 378/97 |
| 5,355,398 A | 10/1994 | Nakano et al. ................. | 378/39 |
| 6,196,715 B1 | 3/2001 | Nambu et al. ............... | 378/197 |
| 6,341,156 B1 | 1/2002 | Baetz et al. ................. | 378/98.8 |
| 6,851,851 B1 * | 2/2005 | Smith et al. ................. | 378/189 |

FOREIGN PATENT DOCUMENTS

| | | |
|---|---|---|
| JP | 3-224545 | 10/1991 |
| JP | 6-181 | 1/1994 |
| JP | 10-295680 | 11/1998 |
| JP | 2000-166909 | 6/2000 |
| JP | 2000-237177 | 9/2000 |
| JP | 2002-028155 | 1/2002 |

* cited by examiner

*Primary Examiner*—Courtney Thomas
*Assistant Examiner*—Hoon Song
(74) *Attorney, Agent, or Firm*—Morgan & Finnegan L.L.P.

(57) ABSTRACT

An apparatus for radiographing an object using radiation from a movable radiation source, includes a detection unit which detects a radiation image of an object, a supporting unit which supports the object, and a control unit which controls a movement of at least one of the detection unit and the supporting unit, based on information of a position of the radiation source and a part to be radiographed of the object, such that a projection image of the part to be radiographed can be detected by the detection unit.

6 Claims, 8 Drawing Sheets

FIG. 3

| BODY PART TO BE RADIOGRAPHED | RADIOGRAPHING THICKNESS | RADIOGRAPHING WIDTH |
|---|---|---|
| CHEST | 20cm | 40cm |
| KNEE | 8cm | 20cm | ns
RADIOGRAPHING APPARATUS AND METHOD

FIELD OF THE INVENTION

The present invention relates to radiography such as tomography.

BACKGROUND OF THE INVENTION

As a technique of associating body parts information and a system with each other in a tomograph, Japanese Patent Laid-Open No. 3-224545 discloses a tomograph which moves an X-ray tube and film in synchronized with each other and performs tomography on a predetermined slice of an object to be radiographed. The tomograph comprises a distance measurement means which is arranged near the X-ray tube and measures the distance to the surface of an object, and a control means which obtains the object thickness from the measured distance and automatically sets a radiographing condition from the object thickness and a set a body part to be radiographed. The radiographing condition is an X-ray exposure condition.

Many modifications to the tomograph are disclosed in Japanese Patent Laid-Open No. 10-295680. Tomographs include one in which the detector is not always moved but is fixed and only the tube is moved, and one in which only an object to be radiographed is moved without moving the detector and tube. By moving the object, the detector and tube for which it is difficult to control need not be moved in synchronized with each other, avoiding degradation in the image quality of a tomographic image caused by synchronous control. In addition, a complicated control mechanism and control circuit for synchronous control can be omitted, reducing the manufacturing cost of the tomograph.

Also in an X-ray stereography and apparatus disclosed in Japanese Patent Laid-Open No. 2000-237177, an-X-ray detector 14 is fixed, and only the X-ray tube is moved. In this moving method, the X-ray tube need not move around an object to be radiographed. The X-ray stereogram of a patient can be obtained while he/she is standing as if he/she were taking fluoroscopy of chest. Unlike a conventional X-ray CT apparatus, the necessity for ensuring a space where the X-ray tube moves or the necessity for a mechanism which conveys a patient into the apparatus while keeping him/her laid can be obviated. The installation area of the apparatus can, therefore, be greatly reduced.

Japanese Patent Registration No. 03149268 discloses various types of imaging apparatuses for forming dental slice images. For example, in type A, both the X-ray generator and X-ray detection surface are moved without moving the support with respect to a slice. In type B, the support is linearly moved parallel to the slice, and at least either the X-ray generator or X-ray detection surface is moved. In type B, only the X-ray detection surface is moved without moving the X-ray generator with respect to the support, like type C, or only the X-ray generator is moved with respect to the support without moving the X-ray detection surface, like type D.

As described above, in the conventional tomograph, an X-ray tube and detector for tomography, and efficient motion of an object to be radiographed are disclosed. However, the X-ray tube, detector, and object are not moved in accordance with the body part to be radiographed.

The tomograph radiographs various body parts with various radiographing sizes. If the detector is moved without considering the size of the body part to be radiographed, the movable portion of the apparatus becomes unnecessarily large, and a wide operating range must be ensured.

A large moving amount takes a long time for positioning a movable portion, decreasing the radiographing efficiency.

When a wide radiographing range is ensured, a body part other than the original body part to be radiographed also exposes to X-rays, which is not preferable in term of reduction in the influence on a human body.

SUMMARY OF THE INVENTION

The present invention has been proposed to solve the conventional problems, and has as its object to provide an excellent radiographic technique.

To solve the above-mentioned problem, the apparatus and the method include the following configuration.

According to the first aspect of the present invention, an apparatus for radiographing an object using radiation from a movable radiation source, comprises:

a detection unit which detects a radiation image of an object;

a supporting unit which supports the object; and a control unit which controls a movement of at least one of the detection unit and the supporting unit, based on information of a position of the radiation source and a part to be radiographed of the object, such that a projection image of the part to be ragiographed can be detected by the detection unit.

According to the second aspect of the present invention, a method for an apparatus for radiographing an object, including a detection unit which detects a radiation image of an object and a supporting unit which supports the object, using radiation from a movable radiation source, comprises the steps of:

generating information of a position of at least one of the detection unit and the supporting unit, based on information of a position of the radiation source and a part to be radiographed of the object, such that a projection image of the part to be radiographed can be detected by the detection unit; and controlling a movement of the least one of the detection unit and the supporting unit, based on the position information generated in the generating step.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 3 is a table showing an example of data arrangement stored in a body parts information table 230;

FIGS. 5A and 5B are views for explaining radiographing of a target (object) in the radiographing apparatus, in which FIG. 5A shows radiographing of a small object, and FIG. 5B shows radiographing of a large object;

DETAILED DESCRIPTION OF THE PREFERRED EMBODIMENTS

Preferred embodiments of the present invention will now be described in detail in accordance with the accompanying drawings.

First Embodiment

Figure 1:
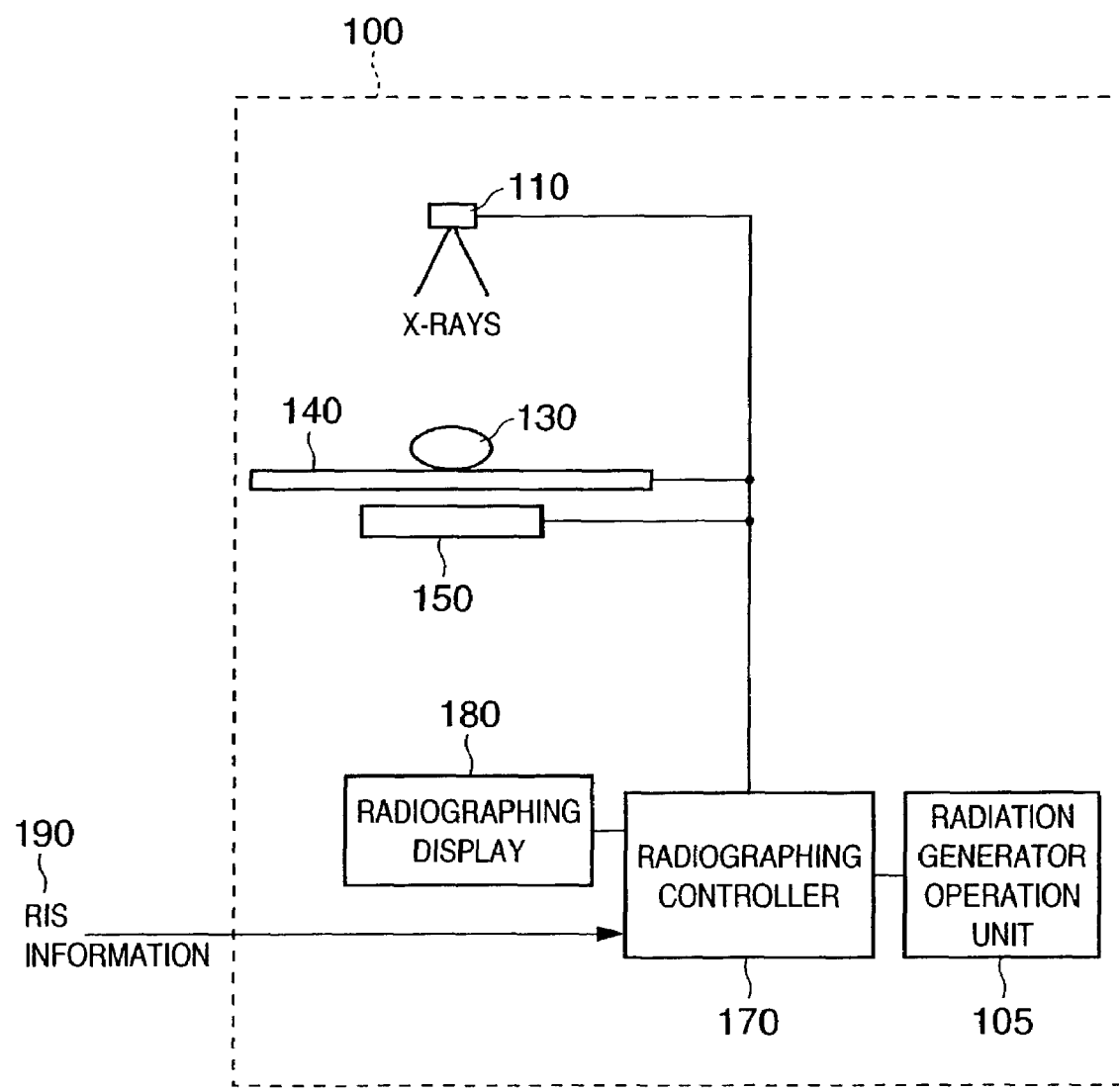
FIG. 1 is a schematic view showing the arrangement of a radiographing apparatus.

FIG. 1 is a schematic view showing the arrangement of a radiographing apparatus.

Reference numeral 100 denotes a radiographing apparatus main body; 105, a radiation generator operation unit; 110, a radiation generator; 130, an object which is irradiated with radiation and radiographed; 140, a radiographing gantry which supports the object 130; 150, a detector which detects object information from emitted X-rays; 170, a radiographing controller; 180, a radiographing display which displays radiographing information; and 190, RIS information which is input from a radiology information system (RIS).

RIS information is information which is transmitted via a network by the radiology information system constructed in a hospital. This information contains pieces of information such as an identification ID for specifying an imaging apparatus, a body part to be radiographed, a radiographing condition, and an object to be radiographed. These pieces of information are transferred to the radiographing controller 170 which receives RIS information via a network.

An operator can set radiographing information by using the radiation generator operation unit 105 and radiographing display 180. The radiation generator operation unit 105 and radiographing display 180 comprise input units (not shown) such as a touch panel and keyboard, and allow selecting and inputting the body part to be radiographed and any information.

The radiographing apparatus can automatically set information on the radiographing body part on the basis of radiographing request information (RIS information 190) received via the above-mentioned RIS. The body part to be radiographed can be set by the operator via the radiation generator operation unit 105 and radiographing display 180.

The radiographing controller 170 drives the radiation (X-ray) generator 110, detector 150, and radiographing gantry 140 to predetermined positions on the basis of the set information on the body part to be radiographed. When the radiographing apparatus is set in an imageable state upon the completion of positioning, the object 130 is irradiated with X-rays under the control of the radiographing controller 170.

The detector 150 detects information of radiation transmitted through the object 130. According to one method, for example, the detector absorbs the energy of transmitted radiation to form a radiation image (latent image), and the radiation image is visualized by developing processing. According to another method, radiation transmitted through the object is converted into visible light by a scintillator, and the visible light is detected as an electrical signal by a photoelectric converter (not shown). The first embodiment adopts the latter.

Information detected by the detector 150 undergoes image processing by the radiographing controller 170. For example, an electrical signal detected as an electrical signal by the photoelectric converter is A/D-converted and processed as an image signal.

The radiographing controller 170 can save image data which is detected by the detector 150 and processed, and transmit the data as the RIS information 190 and the like to a device in a network.

Figure 2:
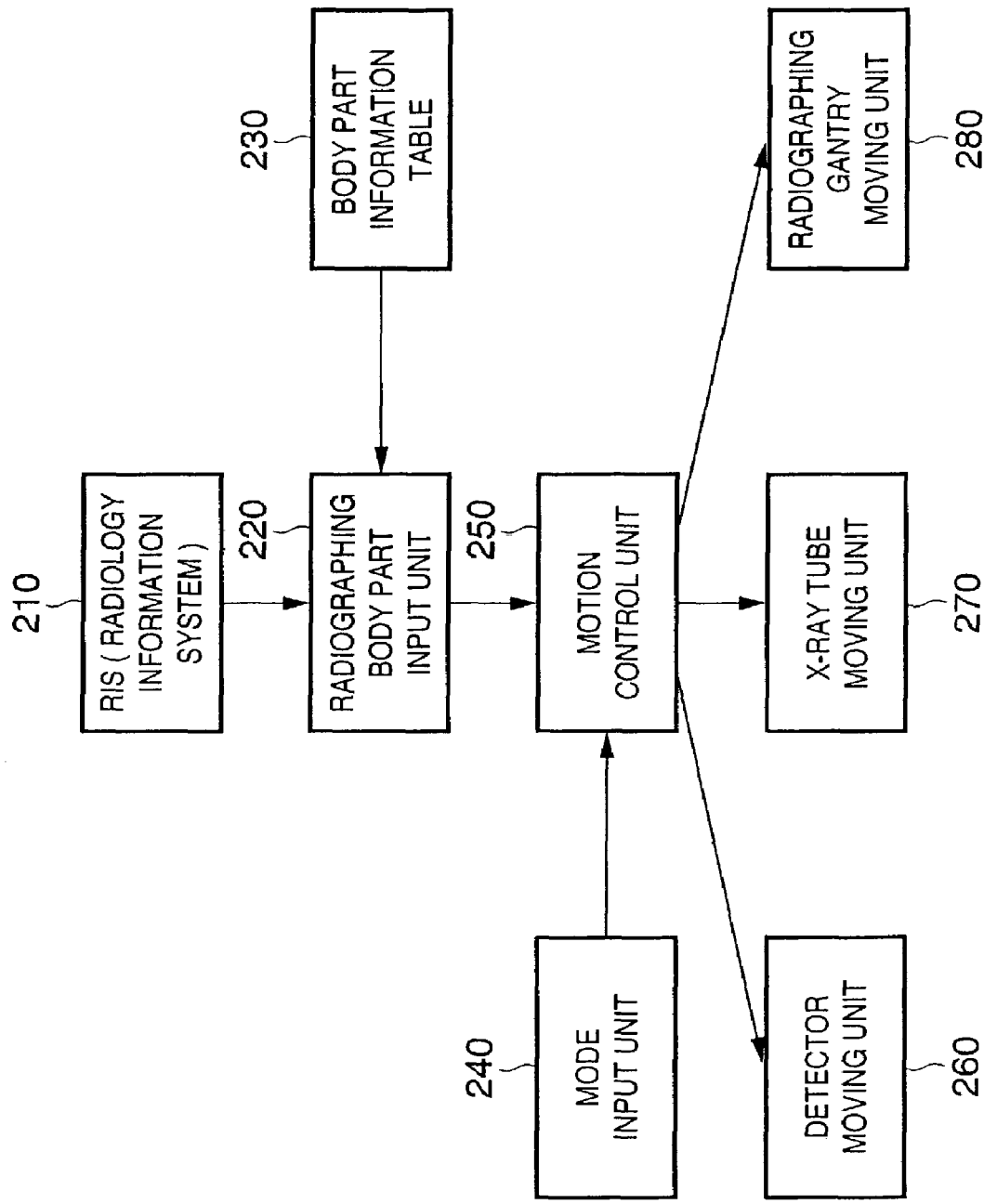
FIG. 2 is a block diagram showing the detailed arrangement of a radiographing controller 170 in the radiographing apparatus.
Figure 7:
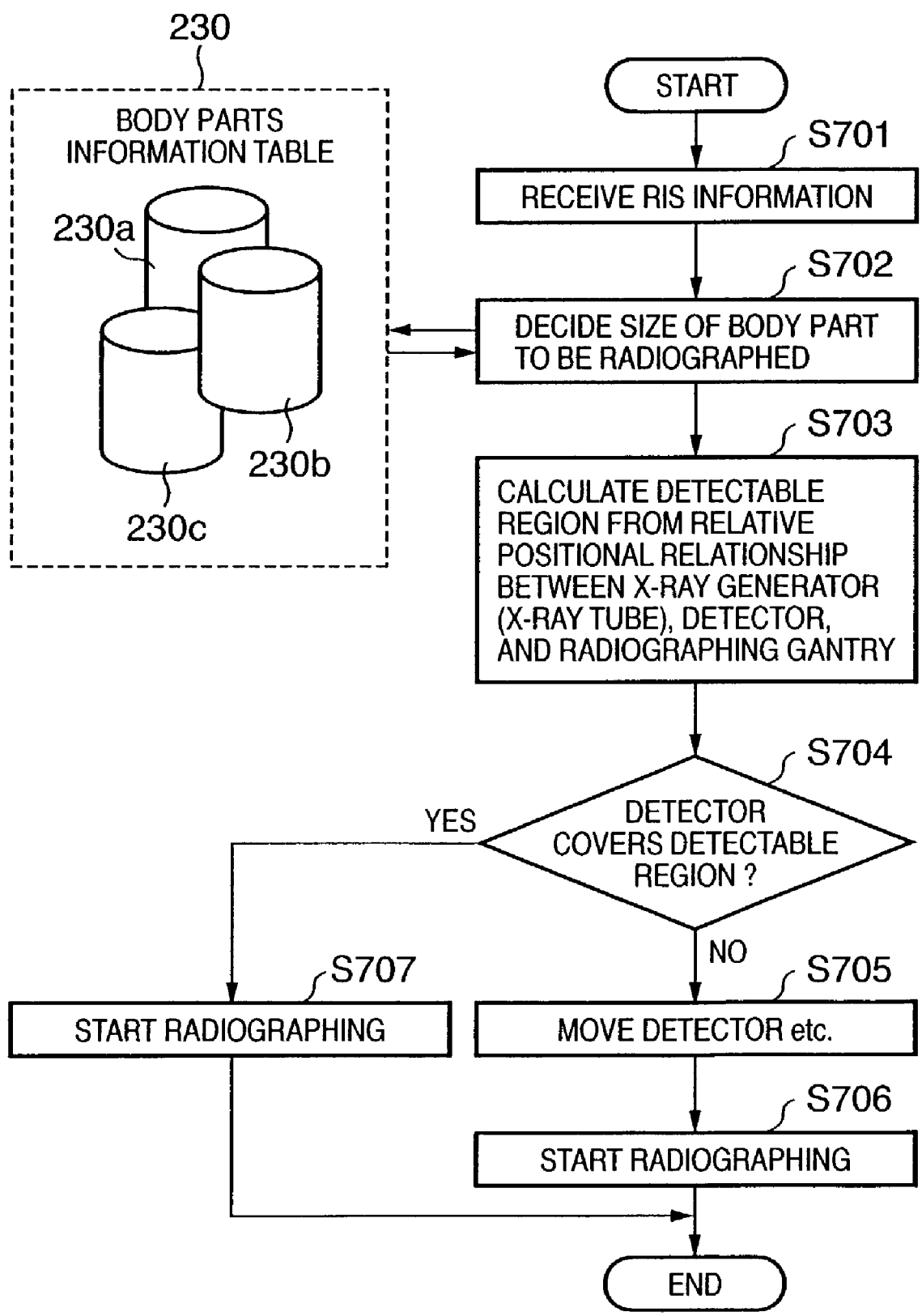
FIG. 7 is a flow chart for explaining the control flow of a radiographing apparatus.

FIG. 2 is a block diagram showing the detailed arrangement of the radiographing controller 170 in the radiographing apparatus. FIG. 7 is a flow chart for explaining the control flow of the radiographing apparatus. If a radiographing request (RIS information 190) is received from a radiology information system 210 via a network (S701), a radiographing body part input unit 220 extracts "body part to be radiographed" and "radiographing condition" contained in the RIS information 190. On the basis of this information, the radiographing body part input unit 220 acquires information on the size of the body part to be radiographed from body parts information table 230 (S702).

Information on the size of the body part to be radiographed is stored in the body parts information table 230 as "thickness" and "width" data of an object to be radiographed. FIG. 3 is a table showing an example of a data arrangement stored in the body parts information table 230. The body parts information table 230 has at least information on the thickness and width of body parts to be radiographed. If the body part to be radiographed is designated from radiographing request information extracted from the RIS information 190, the "thickness" and "width" of the body part can be specified.

Information on the thickness and width that is set in the body parts information table 230 shown in FIG. 3 exhibits a numerical value for an ordinary adult. As the type of data, a plurality of types of tables (230a to 230c) such as a child table and a table corresponding to patient age information in addition to an adult table can be prepared and switched in accordance with the contents of radiographing request information.

The radiographing body part input unit 220 inputs, to a motion control unit 250, radiographing size information acquired on the basis of the body part to be radiographed. Based on this information, the motion control unit 250 calculates the detectable region of a radiation image with respect to the relative positional relationship between the X-ray generator 110 and the radiographing gantry 140 (S703).

Depending on the object size, radiographing information of the object cannot be satisfactorily detected from the relative positional relationship between the X-ray generator (X-ray tube) and the detector. To prevent this, the motion control unit 250 executes control of radiographing the object 130 on the radiographing gantry 140 while moving an X-ray tube 410, the radiographing gantry 140, the detector 150, or a combination of them, (FIG. 4).

Figure 4:
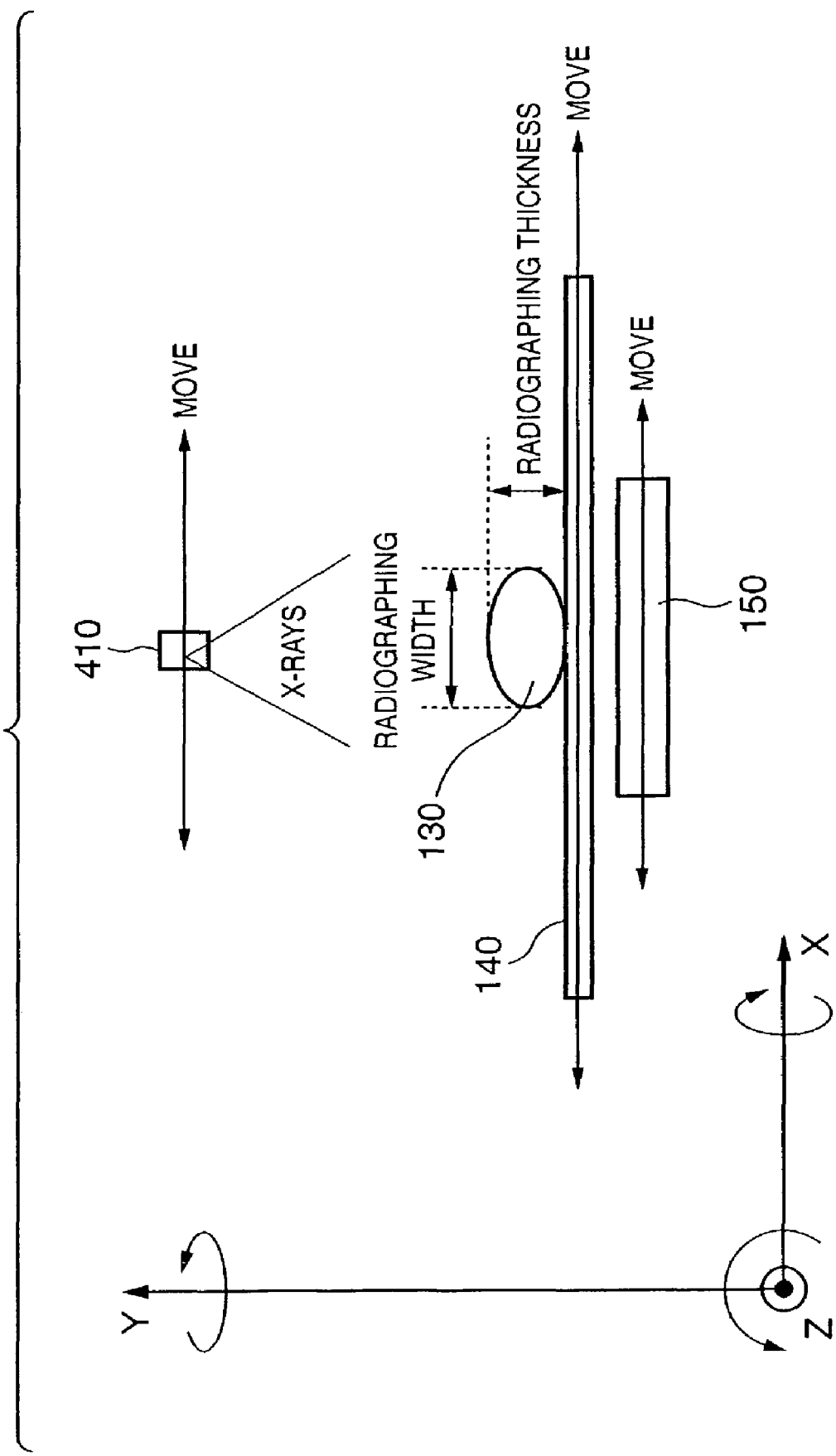
FIG. 4 is a view schematically showing a state in which an X-ray tube 410, radiographing gantry 140, and detector 150 are respectively moved and positioned.

FIG. 4 is a view schematically showing a state in which the X-ray tube 410, radiographing gantry 140, and detector 150 are respectively moved and positioned. Each unit can be moved and positioned in translational and rotational directions defined by the coordinate system.

If the detector 150 covers the detectable region as a result of calculation in step S703 of FIG. 7 (YES in S704), the processing advances to step S707 to start radiographing (S707). If the detector 150 does not cover the detectable region (NO in S704), whether the detector 150 or the like must be moved is decided on the basis of the size of the body part to be radiographed that is decided by processing of step S702. For example, a proper movement mode is decided from movement of only the X-ray tube 410, interlocked movement of the X-ray tube 410 and detector 150, movement of the radiographing gantry 140, and the like. The detector 150 or the like is then moved by a predetermined amount (S705). A region detectable by the detector 150 is ensured, and radiographing starts (S706).

Figure 5A:
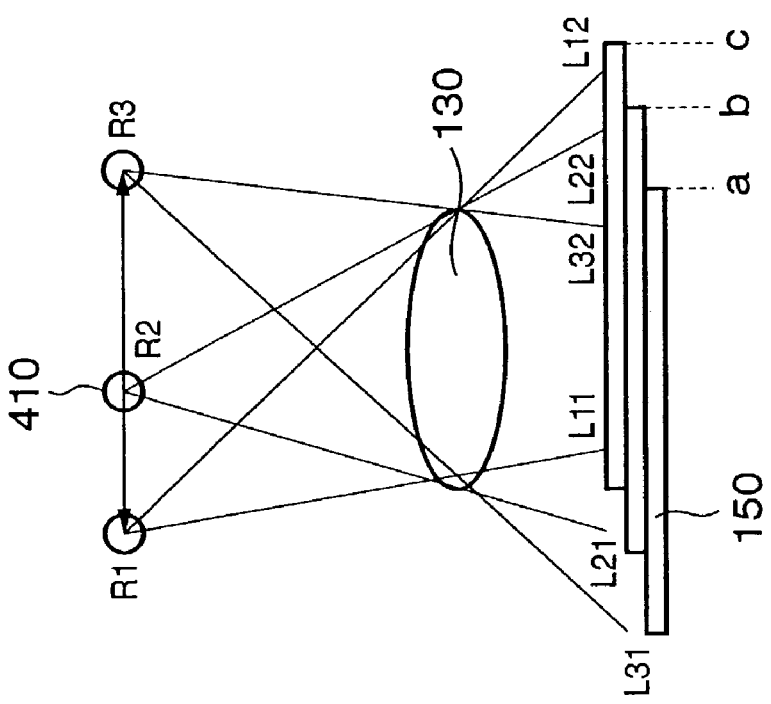
Figure 5B:
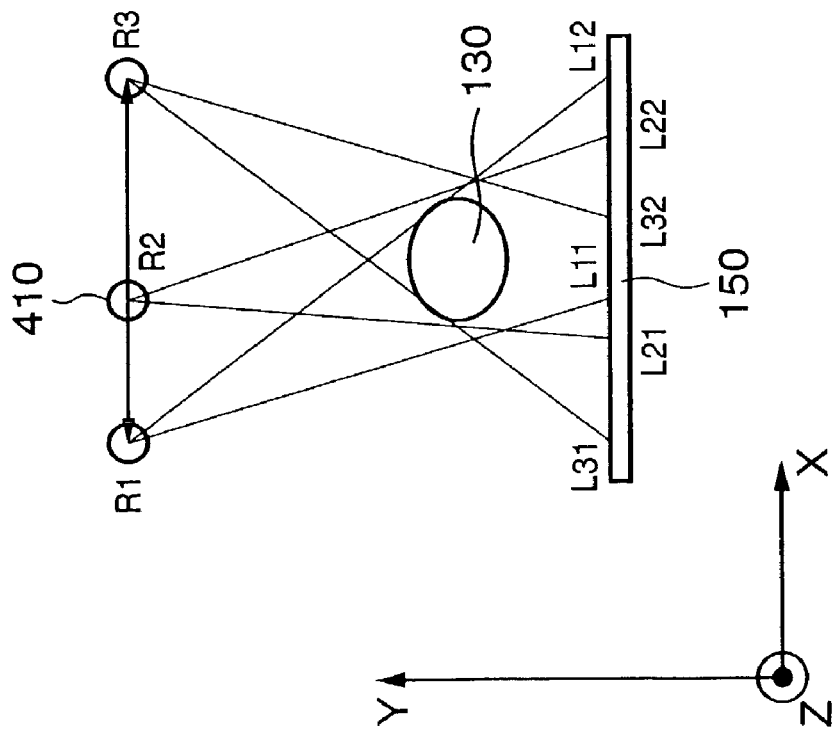

FIGS. 5A and 5B are views for explaining radiographing of a target (object) in the radiographing apparatus according to the present invention. FIG. 5A shows radiographing of a small object, and FIG. 5B shows radiographing of a large object.

In FIG. 5A, X-rays emitted from a position R1 of the X-ray tube can be detected within the range of a position L11 to a position L12 on the detector 150. X-rays emitted from a position R2 of the X-ray tube can be detected within the range of a position L21 to a position L22 on the detector. Similarly, X-rays emitted from a position R3 of the X-ray tube can be detected within the range of a position L31 to a position L32 on the detector. For a small object, the entire movement area of the radiation image of the object can be covered by moving only the X-ray tube. In this case, the detector 150 need not be moved.

To the contrary, for a large object (FIG. 5B), movement of only the X-ray tube cannot ensure a necessary detection region. The detector 150 must be moved together with the X-ray tube to widen the detection range.

More specifically, information obtained by irradiating the object with X-rays from the position R1 of the X-ray tube is detected within the range of the position L11 to the position L12 on the detector 150. In this case, the detector position is (c) along the X-axis.

Information obtained by emitting X-rays from the position R2 of the X-ray tube is detected within the range of L21 to L22 on the detector. In this case, if the detector position is kept fixed at the position (c) along the X-axis, detection information corresponding to the range of the position L21 to the position L11 cannot be detected. For this reason, the position of the detector 150 is moved to (b). In FIG. 5B, the detector positions (a) to (c) are superposed for easy understanding of the motion of the detector. In practice, the detector moves within the same plane.

X-rays emitted from the position R3 of the X-ray tube are detected within the range of the position L31 to the position L32 on the detector 150. In this case, if the detector 150 is kept fixed at the position (b), detection information corresponding to the range of L31 to L21 cannot be detected. Hence, the detector 150 is moved to (a).

The object size can be acquired from the body parts information table on the basis of information on the body part to be radiographed that is extracted from RIS information. Movement of the detector 150 is controlled on the basis of the radiographing size, thereby ensuring an emitted X-ray detection range which covers the body part to be radiographed. In moving the detector 150, the detector may be continuously moved to ensure a predetermined detection range. Alternatively, as shown in FIG. 5B, the detector 150 may be moved to the positions (a), (b), and (c) step by step to ensure the radiographing range.

FIG. 5B illustrates the relative positional relationship between the X-ray tube and the detector for descriptive convenience. The motion control unit 250 can control to move the radiographing gantry 140 with the object 130 or move a combination of the radiographing gantry 140 and detector 150, thereby ensuring the detection range.

Figure 6:
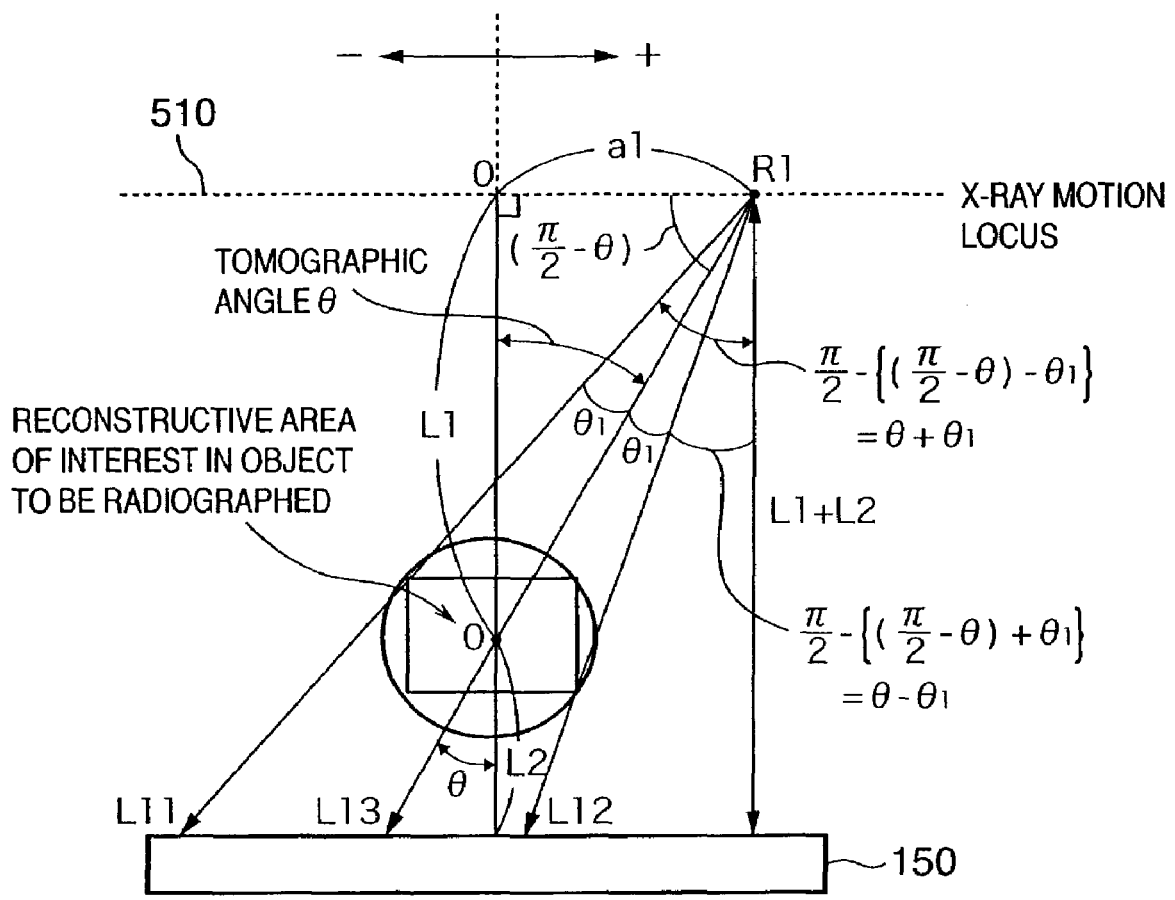
FIG. 6 is a view for explaining calculation of a detection position when movement of an X-ray generator (X-ray tube) and detector in FIG. 5B are controlled in synchronism with each other.

Movement control of the X-ray generator 110, radiographing gantry 140, and detector 150 by the motion control unit 250 will be explained with reference to FIG. 6. FIG. 6 is a view for explaining calculation of the detection position when movement of the X-ray generator (X-ray tube 410) and detector 150 in FIG. 5B are controlled in synchronism with each other.

In FIG. 6, the object 130 is represented by a circle, and a rectangular region (to be referred to as a "reconstructive area of interest" hereinafter) is set in the circle. The X-ray tube 410 moves on an X-ray motion locus 510, and emits X-rays to the object from the position R1.

Let a tomographic angle $\theta$ be the angle defined by an X-ray incident on the center (point O) of the reconstructive area of interest from the X-ray tube and an almost vertical direction, and ($\theta 1$) be the irradiation angle of X-rays which cover the entire reconstructive area of interest by using the angle $\theta$ as a center. The detection position of the detector is given by $$L11 = -(L1+L2) \times \tan(\theta+\theta 1) + a1 \qquad (1)$$

$$L12 = a1 - (L1+L2) \times \tan(\theta-\theta 1) \qquad (2)$$

$$L13 = -L2 \times \tan\theta \qquad (3)$$

(point O on the X-ray motion locus serves as a reference: this calculation corresponds to step S703 in FIG. 7).

After the size of the body part to be radiographed of the object is specified and the tomographic angle $\theta$ is determined, the position of the detector 150 can be obtained. Whether the detector 150 covers the region necessary for detection that is calculated by equations (1) to (3) is decided (this processing corresponds to step S704 of FIG. 7). If the detector does not fall within the region necessary for detection that is obtained by L11 to L12 (NO in S704), the detector 150 is moved by an amount by which the detector 150 deviates from the region, thus ensuring a region where the detector 150 can detect the object 130 (this processing corresponds to step S705 of FIG. 7). In this case, the detector 150 may be moved to (a), (b), and (c) by determining the moving amount of each step, as shown in FIG. 5B (this processing will be explained with reference to FIG. 8). Alternatively, the detector 150 may be moved continuously by a predetermined amount. Data almost free from a radiographing blur caused by movement can be obtained by moving the X-ray tube 410 and detector 150 in cooperation with each other unless X-rays are emitted during movement of the detector 150.

The radiographing controller 170 further comprises a mode input unit 240. The mode input unit 240 sets, on the basis of input information, whether to move the X-ray tube and detector in synchronism with each other, to move the radiographing gantry bearing the object, or alternately move them, and the like. These modes can be automatically set on the basis of radiographing request information (RIS information 190). Alternatively, the operator can set a mode via the radiation generator operation unit 105 or radiographing display 180.

The mode input unit 240 in FIG. 2 can automatically decide a moving mode from information on the body part to be radiographed. That is, for the body part having a large radiographing width such as a chest, movement of the radiographing gantry is disadvantageous because the moving range is large and the movable space of the apparatus is large. However, for the body part having a small radiographing width such as a knee, movement of the radiographing gantry facilitates radiographing rather than movement of the X-ray tube because the moving range is small.

The motion control unit 250 outputs, to a detector moving unit 260, X-ray tube moving unit 270, and radiographing gantry moving unit 280, motion control information corresponding to a control mode which is set by calculating the detectable range on the basis of mode information set by the mode input unit 240 and the radiographing size. The detector moving unit 260, X-ray tube moving unit 270, and radiographing gantry moving unit 280 move the detector 150, the X-ray tube 410, and the radiographing gantry 140 to each position necessary for detection of a radiation image on the basis of the motion control information calculated by the motion control unit 250.

As described above, the radiographing apparatus according to the present embodiment can decide a region to be radiographed on the basis of information of the body part to be radiographed, move the detector or the like on the basis of the decision, and radiograph an object.

Since a necessary radiographing range can be set in accordance with information of the body part to be radiographed, the movable portion of the apparatus can be minimized to complete positioning of the movable portion within a short time.

Since a necessary radiographing range can be set on the basis of information of the body part to be radiographed, irradiation of an object with X-rays can be limited to a range necessary for radiographing.

Second Embodiment

In processing of FIG. 7, a detection range is calculated from information on the size of the body part to be radiographed (FIG. 6 and step S703 of FIG. 7), and movement of the detector 150 is controlled. However, the present invention is not limited to the method of individually calculating a detection range and successively obtaining a moving amount. It is also possible to set a moving amount corresponding to the body part to be radiographed in advance, set the moving amount of each step, and control motion of the detector (FIG. 8).

Figure 8:
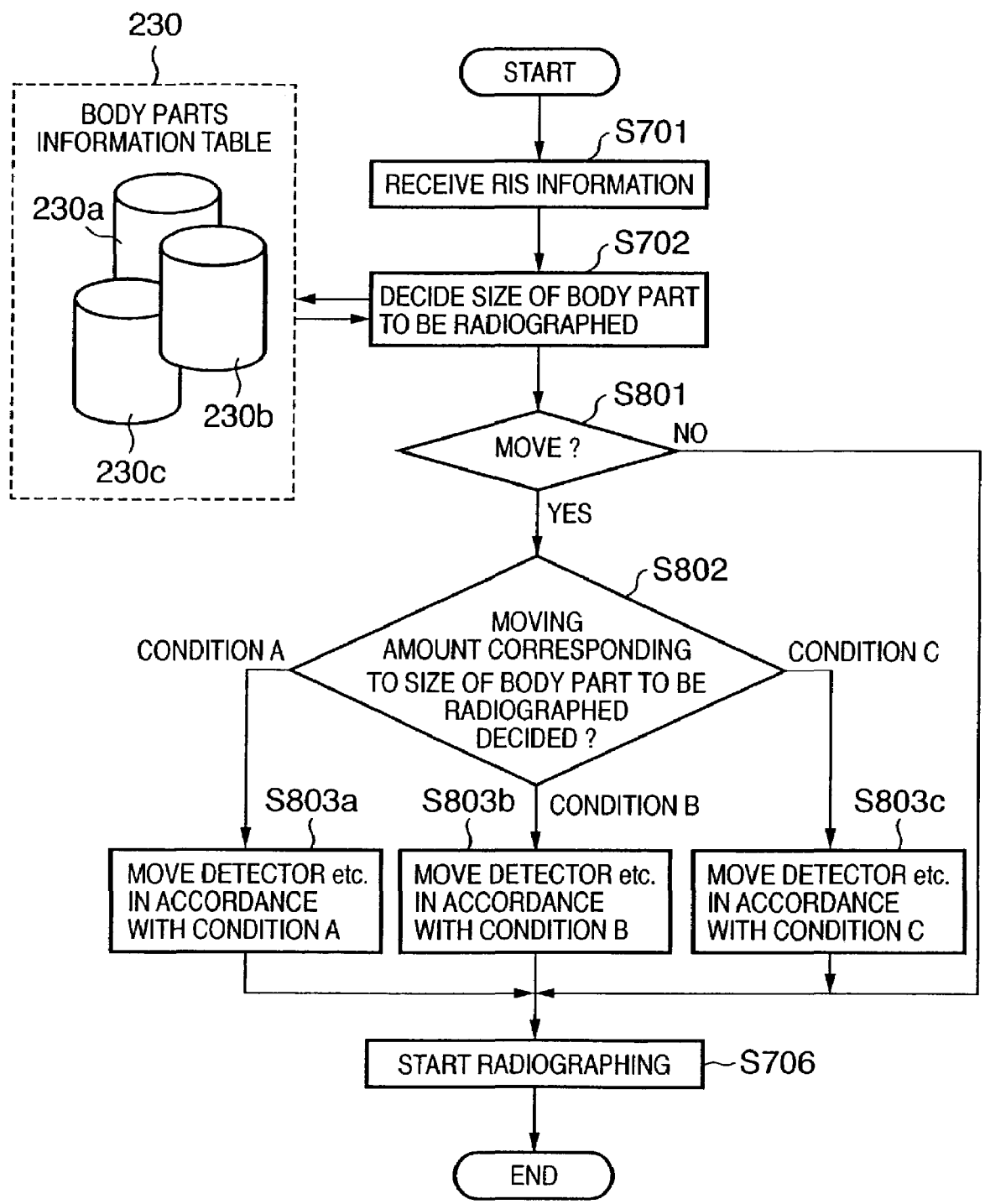
FIG. 8 is a flow chart for explaining the control flow of the radiographing apparatus according to the second embodiment.

FIG. 8 is a flow chart for explaining the control flow of a radiographing apparatus according to the second embodiment. The same step numbers denote the same processes as those in the flow chart of FIG. 7.

In step S801 of FIG. 8, whether a detector 150 or the like must be moved is decided on the basis of the size of the body part to be radiographed that is decided by processing of step S702 described above. For example, a proper movement mode is decided from movement of only an X-ray tube 410, interlocked movement of the X-ray tube 410 and detector 150, movement of a radiographing gantry 140, and the like.

If the detector need not be moved (NO in S801), the processing advances to step S706 to start radiographing.

If the detector or the like must be moved (YES in S801), the processing advances to step S802 to decide a moving amount corresponding to the size of the body part to be radiographed (S802).

For example, to radiograph a "chest" as the body part having a large radiographing width, the detector position is moved to the position (a) shown in FIG. 5B (S803a). To radiograph a "knee" as the body part having a small radiographing width, the detector position is moved to the position (b) shown in FIG. 5B (S803b or S803c). It is also possible to set moving amounts corresponding to the sizes of the body parts to be radiographed in a radiographing controller 170 in advance, and selectively set the moving amount in accordance with the size of the body part to be radiographed of the object (S803a to S803c).

In step S802, relationships between the sizes of the body parts to be radiographed and moving amounts are classified into three conditions. Which of following conditions (A) to (C) corresponds to the size of the body part to be radiographed that is decided by processing of step S702 is decided.

Condition (A):

$$\text{radiographing reference value (large)} \leq \text{size of body part to be radiographed} \quad (4)$$

Condition (B):

$$\text{radiographing reference value (small)} \leq \text{size of body part to be radiographed} < \text{radiographing reference value (large)} \quad (5)$$

Condition (C):

$$\text{size of body part to be radiographed} \leq \text{radiographing reference value (small)} \quad (6)$$

In equalities (4) to (6), the radiographing reference values (large) and (small) are reference values set in advance in a memory (not shown) such as a ROM in the radiographing controller 170. For descriptive convenience, sizes are classified into the three conditions. However, finer condition decision may be executed.

The detector 150, the X-ray tube 410, the radiographing gantry 140, or a combination of them are moved in accordance with a condition selected on the basis of the decision result in step S802 (S803a to S803c). Movement of the detector 150 or the like is controlled by a motion control unit 250. The moving amount is controlled in accordance with each of the conditions of inequalities (4) to (6).

After positioning to a predetermined position is completed, radiographing starts (S706). According to the second embodiment, a preset moving amount is selectively set in accordance with information on the body part to be radiographed without individually calculating a detection range. The detector or the like can be moved within a short time.

As described above, the radiographing apparatus according to the second embodiment can decide a region to be radiographed on the basis of information on the body part to be radiographed, select the movement mode of the detector or the like on the basis of the decision, and radiograph an object.

Since the movement mode of the detector or the like can be set on the basis of information on the body part to be radiographed, positioning of a movable portion can be completed within a short time.

Since the movement mode of the detector or the like can be set on the basis of information on the body part to be radiographed, irradiation of an object with X-rays can be limited to a range necessary for radiographing.

Other Embodiment

The object of the present invention is also achieved when a storage medium which stores software program codes for realizing the functions of an apparatus or system according to either of the first and second embodiments is supplied to the apparatus or system, and the computer (or the CPU or MPU) of the apparatus or system reads out and executes the program codes stored in the storage medium.

In this case, the program codes read out from the storage medium realize the functions of either of the first and second embodiments. The program codes and the storage medium which stores the program codes constitute the present invention.

The storage medium for supplying the program codes includes a ROM, floppy® disk, hard disk, optical disk, magnetooptical disk, CD-ROM, CD-R, magnetic tape, and nonvolatile memory card.

The functions of either of the first and second embodiments are realized when the computer executes the readout program codes. Also, the functions of either of the first and second embodiments are realized when an OS or the like running on the computer performs part or all of actual processing on the basis of the instructions of the program codes.

The functions of either of the first and second embodiments are also realized when the program codes read out from the storage medium are written in the memory of a function expansion board inserted into the computer or the memory of a function expansion unit connected to the computer, and the CPU of the function expansion board or function expansion unit performs part or all of actual processing on the basis of the instructions of the program codes.

When the present invention is applied to the program or the storage medium which stores the program, the program is comprised of, e.g., program codes corresponding to the flow chart shown in FIG. 7 or 8.

As many apparently widely different embodiments of the present invention can be made without departing from the spirit and scope thereof, it is to be understood that the invention is not limited to the specific embodiments thereof except as defined in the claims.

What is claimed is:

1. An apparatus for radiographing, comprising:
   a radiation generation source which irradiates radiation to an object to be radiographed;
   a first movement unit which moves said radiation generation source;
   a detection unit which executes image capturing based on detection of the radiation transmitted through the object;
   a second movement unit which moves said detection unit;
   an input unit which selects a first mode for executing movement of said first movement unit, where said detection unit is fixed to enable image capturing by irradiating the area of the object to be radiographed from a plurality of directions, or a second mode for executing interlocked movement of said first movement unit and said second movement unit; and
   a control unit which controls said radiation generation source, said detection unit, said first movement unit and said second movement unit, based on the first mode or the second mode selected by said input unit.

2. The apparatus according to claim 1, further comprising:
   a supporting unit which supports the object; and
   a third movement unit which moves said supporting unit,
   wherein said input unit selects a third mode for executing interlocked movement of said first movement unit and said second movement unit and said third movement unit.

3. The apparatus according to claim 1, wherein said control unit comprises:
   an information table which stores information on the thickness and width obtained by the image capturing corresponding to the object;
   a moving amount calculation unit which decides whether or not to move said radiation generation source, said detection unit and said supporting unit according to the information on the thickness and the width and at least one of the first mode, the second mode or the third mode selected by said input unit and calculates a moving amount.

4. The apparatus according to claim 1, wherein said control unit calculates a position of at least one of said detection unit and said supporting unit in correspondence with the information of the position of said radiation generation source and the body part information.

5. A method for radiographing an object by using an apparatus including a radiation generation source which irradiates radiation to an object to be radiographed, a first movement unit which moves said radiation generation source, a detection unit which executes image capturing based on detection of the radiation transmitted through the object, a second movement unit which moves said detection unit, comprising steps of:
   selecting a first mode for executing movement of said first movement unit, where said detection unit is fixed to enable image capturing by irradiating the area of the object to be radiographed from a plurality of directions, or a second mode for executing interlocked movement of said first movement unit and said second movement unit; and
   controlling said radiation generation source, said detection unit, said first movement unit and said second movement unit, based on the first mode or the second mode selected in said selecting step.

6. A computer-readable storage medium storing a program which causes a computer to execute a method for radiographing an object by using an apparatus including a radiation generation source which irradiates radiation to an object to be radiographed, a first movement unit which moves said radiation generation source, a detection unit which executes image capturing based on detection of the radiation transmitted through the object, a second movement unit which moves said detection unit, the method comprising steps of:
   selecting a first mode for executing movement of said first movement unit, where said detection unit is fixed to enable image capturing by irradiating the area of the object to be radiographed from a plurality of directions, or a second mode for executing interlocked movement of said first movement unit and said second movement unit; and
   controlling said radiation generation source, said detection unit, said first movement unit and said second movement unit, based on the first mode or the second mode selected in said selecting step.

* * * * *